US012747971B2

(12) United States Patent
Hughes et al.

(10) Patent No.: US 12,747,971 B2
(45) Date of Patent: Sep. 29, 2026

(54) FLOW RATE DETECTION FOR AN ASPIRATING SMOKE DETECTION SYSTEM

(71) Applicant: Honeywell International Inc., Charlotte, NC (US)

(72) Inventors: Aleksis Terence Hughes, Yallambie (AU); Michael Anthony De Looper, Narre Warren (AU); Elizabeth Chai, Malvern East (AU)

(73) Assignee: Honeywell International Inc., Charlotte, NC (US)

( * ) Notice: Subject to any disclaimer, the term of this patent is extended or adjusted under 35 U.S.C. 154(b) by 412 days.

(21) Appl. No.: 18/230,817

(22) Filed: Aug. 7, 2023

(65) Prior Publication Data

US 2025/0052600 A1 Feb. 13, 2025

(51) Int. Cl.

| | |
|---|---|
| ***G01F 1/58*** | (2006.01) |
| ***G01F 1/32*** | (2022.01) |
| ***G01F 1/325*** | (2022.01) |
| ***G01N 1/14*** | (2006.01) |
| ***G01N 15/00*** | (2024.01) |
| ***G01N 33/00*** | (2006.01) |
| ***G01P 5/00*** | (2006.01) |
| ***G08B 17/113*** | (2006.01) |

(52) U.S. Cl.

CPC ......... *G01F 1/586* (2013.01); *G01N 33/0027* (2013.01); *G01F 1/3209* (2013.01); *G01F 1/3266* (2022.01); *G01N 1/14* (2013.01); *G01N 15/00* (2013.01); *G01P 5/00* (2013.01); *G08B 17/113* (2013.01)

(58) Field of Classification Search

CPC ...... G01F 1/586; G01F 1/3209; G01F 1/3266; G01N 33/0027; G01N 1/14; G01N 15/00; G08B 17/113; G01P 5/00

USPC ........................................................ 73/31.05

See application file for complete search history.

(56) References Cited

U.S. PATENT DOCUMENTS

| | | | | |
|---|---|---|---|---|
| 4,123,940 | A * | 11/1978 | Herzl | G01F 15/063 73/861.24 |
| 5,443,552 | A | 8/1995 | Tomita | |
| 6,351,999 | B1 | 3/2002 | Maul et al. | |
| 6,626,048 | B1 * | 9/2003 | Dam Es | G01F 1/586 73/861.15 |
| 9,027,418 | B2 | 5/2015 | Smith et al. | |
| 10,365,134 | B2 | 7/2019 | Bogdanov et al. | |
| 10,416,009 | B1 | 9/2019 | Miller et al. | |

(Continued)

FOREIGN PATENT DOCUMENTS

| | | | |
|---|---|---|---|
| CN | 113067495 | A | 7/2021 |
| EP | 3990869 | A1 | 5/2022 |

(Continued)

*Primary Examiner* — Peter J Macchiarolo

*Assistant Examiner* — John M Royston

(74) *Attorney, Agent, or Firm* — Brooks, Cameron & Huebsch, PLLC

(57) ABSTRACT

Methods, devices, and systems for flow rate detection for an aspirating smoke detection system are described herein. One device includes a flow rate sensor for an aspirating smoke detection system comprising a flow chamber to allow a gas to flow through the flow chamber and a receive coil located inside the flow chamber, where a processor is to execute instructions to receive a signal from the receive coil and determine a flow rate of gas through the flow chamber based on the signal.

9 Claims, 5 Drawing Sheets

(56) References Cited

U.S. PATENT DOCUMENTS

| | | | | |
|---|---|---|---|---|
| 10,969,258 | B2 | 4/2021 | Bogdanov | |
| 2015/0122009 | A1* | 5/2015 | Berkcan | G01F 25/10 73/204.11 |
| 2015/0128722 | A1 | 5/2015 | Ajay et al. | |
| 2020/0217698 | A1* | 7/2020 | Ciobanu | G01F 1/586 |
| 2021/0140805 | A1* | 5/2021 | Savini | G01F 1/586 |

FOREIGN PATENT DOCUMENTS

| | | | |
|---|---|---|---|
| IN | 202221063690 | | 11/2022 |
| KR | 101595529 | B1 | 2/2016 |
| WO | 2018024984 | A1 | 2/2018 |
| WO | 2020260401 | A1 | 12/2020 |

* cited by examiner

FLOW RATE DETECTION FOR AN ASPIRATING SMOKE DETECTION SYSTEM

TECHNICAL FIELD

The present disclosure relates to methods, devices, and systems for flow rate detection for an aspirating smoke detection system.

BACKGROUND

Facilities (e.g., buildings), such as commercial facilities, office buildings, hospitals, and the like, can have an alarm system that can be triggered during an emergency situation (e.g., a fire) to warn occupants to evacuate. For example, an alarm system may include a control panel (e.g., a fire control panel) and a plurality of aspirating smoke detector devices located throughout the facility (e.g., on different floors and/or in different rooms of the facility) that are included in an aspirating smoke detection system that can detect a hazard event, such as smoke generation (e.g., as the result of a fire or otherwise). The aspirating smoke detector can transmit a signal to the control panel in order to notify a building manager, occupants of the facility, emergency services, and/or others of the hazard event via alarms or other mechanisms.

DETAILED DESCRIPTION

Figure 1:
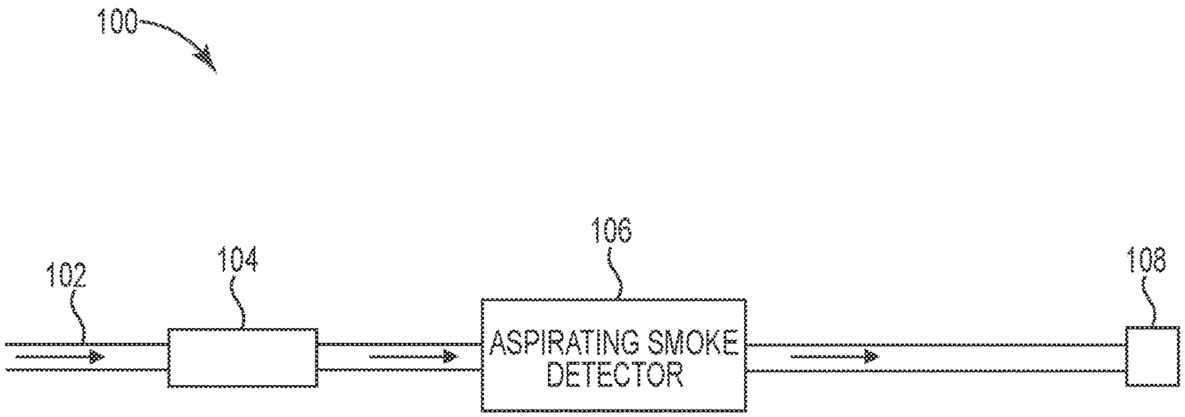
FIG. 1 is an aspirating smoke detection system having a flow rate sensor, in accordance with one or more embodiments of the present disclosure.

Methods, devices, and systems for flow rate detection for an aspirating smoke detection system are described herein. One device includes a flow rate sensor for an aspirating smoke detection system comprising a flow chamber to allow a gas to flow through the flow chamber and a receive coil located inside the flow chamber, where a processor is to execute instructions to receive a signal from the receive coil and determine a flow rate of gas through the flow chamber based on the signal.

An aspirating smoke detector device can be utilized as part of an aspirating smoke detection system in a facility to detect a hazard event by detecting the presence of smoke. The aspirating smoke detector device can draw gas (e.g., air, via a blower) from the facility into a sensor through a network of pipes throughout the facility. The network of pipes can comprise a pipe sampling network. The sensor can sample the gas from the pipe sampling network in order to determine whether the gas sampled from the facility includes smoke particles. In response to detection of smoke particles, the aspirating smoke detector device can transmit a signal to a control panel in the facility to signal detection of smoke particles in the area of the facility the aspirating smoke detector is monitoring and sampling gas from.

As mentioned above, in order for the aspirating smoke detector device to sample gas for smoke particles, the gas has to be transported from the sampling location to the aspirating smoke detector device. Accordingly, the aspirating smoke detector device can utilize the network of pipes throughout the facility to transport sampled gas to the aspirating smoke detector device. For example, the pipe sampling network can transport gas from an area of the facility to the aspirating smoke detector device for testing.

In order to ensure the aspirating smoke detector device is correctly sampling the gas, the gas is to flow through the network of sampling pipes to the aspirating smoke detector device at a known flow rate. Determining the flow rate of the gas ensures the aspirating smoke detector device is operating correctly. Additionally, sensing and monitoring the flow rate of the gas through the network of sampling pipes may be a regulatory requirement in certain jurisdictions to ensure safe operation of a facility.

Accordingly, a flow rate sensor can be utilized for flow rate detection for an aspirating smoke detection system. The flow rate sensor can be an easy to manufacture sensor that can be easily implemented in any new or existing aspirating smoke detection system. Such an approach can allow for a cheaper flow rate sensor that is easy to install, as compared with previous approaches.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 108 may reference element "08" in FIG. 1, and a similar element may be referenced as 208 in FIG. 2.

FIG. 1 is an aspirating smoke detection system 100 having a flow rate sensor 104, in accordance with one or more embodiments of the present disclosure. As illustrated in FIG. 1, system 100 can include a pipe sampling network 102, a flow rate sensor 104, an aspirating smoke detector device 106, and a blower 108.

As mentioned above, the system 100 can include a pipe sampling network 102. As used herein, the term "pipe sampling network" refers to a group of pipes configured to take samples of gas at a sampling location and transport the gas from the sampling location to a detector. For example, the pipe sampling network 102 can sample gas at various sampling locations (e.g., not illustrated in FIG. 1 for clarity and so as not to obscure embodiments of the present disclosure) and transport the gas to the aspirating smoke detector device 106 for analysis. The pipe sampling network 102 can include various sampling ports located throughout the pipe sampling network 102. As used herein, the term "port" refers to an aperture in a pipe. The sampling ports can allow for gas to flow from an area in the facility into the pipe sampling network 102.

Although the pipe sampling network 102 is illustrated in FIG. 1 as being a singular pipe, embodiments of the present disclosure are not so limited. For example, the pipe sampling network 102 can include more than one pipe. Additionally, more than one pipe may connect to the aspirating smoke detector device 106.

The system 100 can include a blower 108. As used herein, the term "blower" refers to a mechanical device for moving gas in a particular direction. For example, the blower 108 can be utilized to cause a flow of gas through the pipe sampling network 102 and into the aspirating smoke detector device 106. The blower 108 can, in some instances, comprise a ducted housing having a fan that, when spinning, causes gas (e.g., such as air) to flow in a particular direction.

The system 100 further includes the aspirating smoke detector device 106 that is connected to the pipe sampling network 102. As mentioned above, the aspirating smoke detector device 106 can detect smoke particles within gas sampled from the sampling locations in the facility. A flow rate of gas through the pipe sampling network 102 and into the aspirating smoke detector device 106 can be determined by a flow rate sensor 104, as is further described herein.

As mentioned above, the system 100 includes a flow rate sensor 104. As used herein, the term "flow rate sensor" refers to a device that measures the flow of a fluid. A fluid can be, for example, gas and/or liquid. For example, the flow rate sensor 104 can measure a volume of gas which passes a location per unit of time.

As is further described in connection with FIGS. 2, 3A, and 3B, the flow rate sensor 104 can include a flow chamber connected to the pipe sampling network 102, a coil, and a controller. The flow chamber can be connected to the pipe sampling network 102 such that the flow of gas flows through the flow chamber. Additionally, the controller can be configured to receive a signal from the coil, and determine a flow rate of gas through the flow chamber based on the signal.

For instance, in some examples, the coil is configured to physically oscillate in response to the flow of gas through the flow chamber. Accordingly, the controller is configured to determine a frequency of the signal, the frequency being associated with the physical oscillation of the coil, and determine a flow rate of the gas through the flow chamber based on the frequency, as is further described in connection with FIG. 2.

Further, in some examples, the coil can be connected to a flexible base configured to deflect into the flow of gas in the flow chamber in response to a voltage being applied to the coil. Accordingly, the controller is configured to determine whether an amplitude associated with the voltage exceeds a threshold amplitude amount, and determine, in response to the amplitude exceeding the threshold amplitude amount, a flow rate of the gas through the flow chamber based on the voltage applied to the coil, as is further described in connection with FIGS. 3A and 3B.

Figure 2:
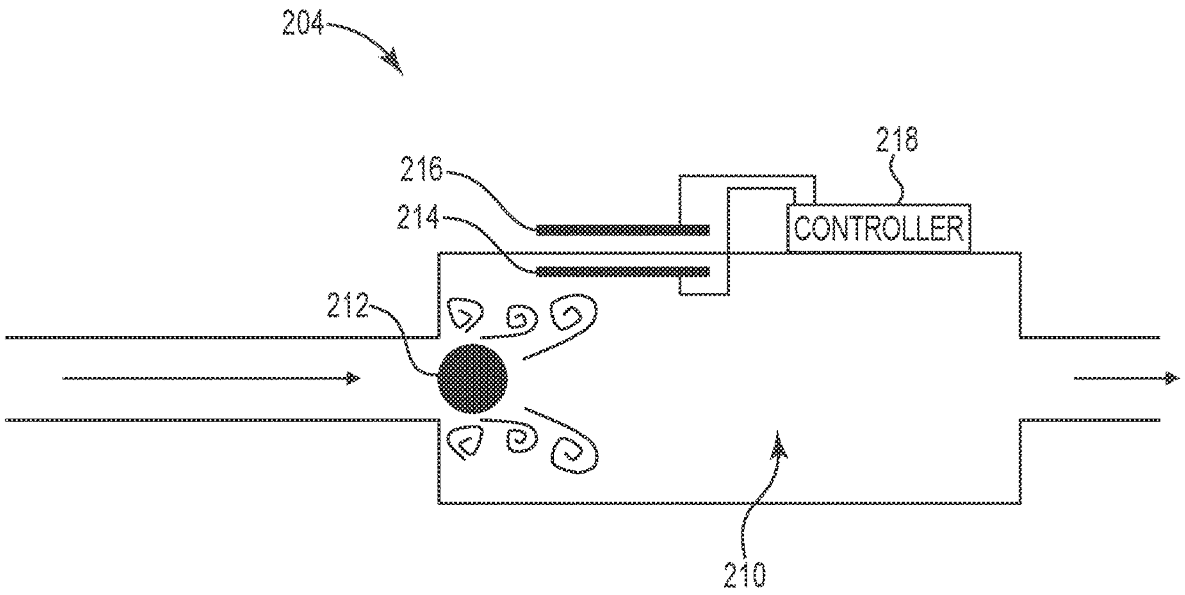
FIG. 2 is a top view of an example of a flow rate sensor having a receive coil and a transmit coil, in accordance with one or more embodiments of the present disclosure.

FIG. 2 is a top view of an example of a flow rate sensor 204 having a receive coil 214 and a transmit coil 216, in accordance with one or more embodiments of the present disclosure. The flow rate sensor 204 can further include a flow chamber 210, a bluff body 212, and a controller 218.

As previously mentioned in connection with FIG. 1, the flow rate sensor 204 can be connected to a pipe sampling network. For example, the flow chamber 210 can be connected to the pipe sampling network such that gas is allowed to flow from the pipe sampling network and through the flow chamber 210 of the flow rate sensor 204.

As the gas enters the flow chamber 210 from the pipe sampling network, the gas can encounter bluff body 212. The bluff body 212 can be located inside the flow chamber 210 and can disrupt the flow of gas through the flow chamber 210. As used herein, the term "bluff body" refers to an object which, as a result of its shape, causes flow separation of a flow of fluid over the body. For example, as the gas flows by the bluff body 212, the bluff body 212 causes the gas flow to separate, resulting in detachment of a boundary layer of the flow from a surface of the bluff body 212 into a wake. In some examples, the bluff body 212 is to cause the gas flowing through the flow chamber 210 to be a turbulent flow in the flow chamber 210.

The flow rate sensor 204 can further include a receive coil 214 located inside the flow chamber 210. The receive coil 214 can be an electrical conductor in the shape of a coil where, upon application of an electric current, the coil can generate a magnetic field. The receive coil 214 can be located on a printed circuit board (PCB). For example, the PCB can be a polyimide PCB on which the receive coil 214 is located.

As illustrated in FIG. 2, the receive coil 214 can be located downstream of the bluff body 212 in the flow chamber 210. Accordingly, the receive coil 214 (e.g., the PCB) can physically oscillate in response to the flow of gas acting upon the receive coil 214. For example, the disrupted (e.g., turbulent) flow of the gas after interaction with the bluff body 212 as the gas flows through the flow chamber 210 can physically act upon (e.g., apply a force in varying magnitude to) the receive coil 214. As a result, the receive coil 214 can oscillate.

In response to the physical oscillation, the receive coil 214 can generate a signal. The signal can be, for example, an amplitude modulated signal.

The flow rate sensor 204 can further include a transmit coil 216. As illustrated in FIG. 2, the transmit coil 216 can also be located downstream of the bluff body 212. The transmit coil 216 can be located outside of the flow chamber 210 and at a same position downstream of the bluff body 212 as the receive coil 214.

Although the transmit coil 216 is illustrated in FIG. 2 as being located outside of the flow chamber 210, embodiments of the present disclosure are not so limited. For example, the transmit coil 216 can be located inside of the flow chamber 210, be integrated within the body of the flow chamber 210, etc.

The transmit coil 216 can be an electromagnet located on a PCB. For example, the transmit coil 216 can be a type of magnet in which a magnetic field is produced by the transmit coil 216 when an electric current is passed through a coil surrounding the magnet.

As illustrated in FIG. 2, the receive coil 214 and the transmit coil 216 can be electrically connected to the controller 218. Accordingly, the receive coil 214 and the transmit coil 216 can transmit signals to and/or receive signals from the controller 218.

The controller 218 can cause an oscillating signal to be applied to the transmit coil 216. Such an oscillating signal can cause the receive coil 214 to generate a signal in response to the physical oscillation of the receive coil 214 (e.g., experienced by the receive coil 214 as a result of the disrupted flow of the gas through the flow chamber 210 caused by the bluff body 212).

The signal generated by the receive coil 214 in response to the physical oscillation of the receive coil 214 can be transmitted to the controller 218. Accordingly, the controller 218 can determine a frequency of the signal generated by the receive coil 214. In order to determine the frequency, the controller 218 can demodulate the signal generated by the receive coil 214.

Once the controller 218 has determined the frequency of the signal generated by the receive coil 214, the controller 218 can determine a flow rate of the gas through the flow chamber 210 based on the frequency of the signal. For example, the controller 218 can include a memory (e.g., not illustrated in FIG. 2 for clarity and so as not to obscure embodiments of the present disclosure). The memory can include a lookup table stored therein. Accordingly, the controller 218 can determine the flow rate by comparing the frequency of the signal to a plurality of frequencies included in the lookup table and determining, based on the frequency matching a particular frequency in the lookup table, the flow rate to be a particular flow rate from the lookup table that is associated with the particular frequency.

For example, the lookup table may include a frequency of 100 Hertz (Hz) with an associated flow rate of 10 Liters per minute (L/m) and a frequency of 150 Hz with an associated flow rate of 15 L/m. In response to the controller 218 determining the frequency to be 400 Hz, the controller 218 can compare the determined frequency (e.g., 400 Hz) to the plurality of frequencies included in the lookup table (e.g., 400 Hz, 500 Hz, etc.) and determine, based on the determined frequency (e.g., 400 Hz) matching a frequency of the plurality of frequencies in the lookup table (e.g., 400 Hz), the flow rate to be 10 L/m.

In some examples, the determined frequency may not match exactly those frequencies of the plurality of frequencies in the lookup table. For instance, the determined frequency may be 412 Hz. In some examples, the controller 218 can determine a frequency of the plurality of frequencies (e.g., 400 Hz) in the lookup table that is the closest to the determined frequency (e.g., 412 Hz), and determine the flow rate to be 10 L/m.

Additionally, in some examples, the closest frequency may not result in the accuracy desired and/or mandated in determining the flow rate. In some examples, the controller 218 can interpolate between those frequencies of the plurality of frequencies in the lookup table to determine an exact flow rate. For example, the determined frequency may be 412 Hz, and the controller 218 can interpolate, using the two closest frequencies of the plurality of frequencies (e.g., 400 Hz and 500 Hz) to the determined frequency, to determine the flow rate associated with the 412 Hz frequency to be approximately 10.6 L/m.

Figure 3A:
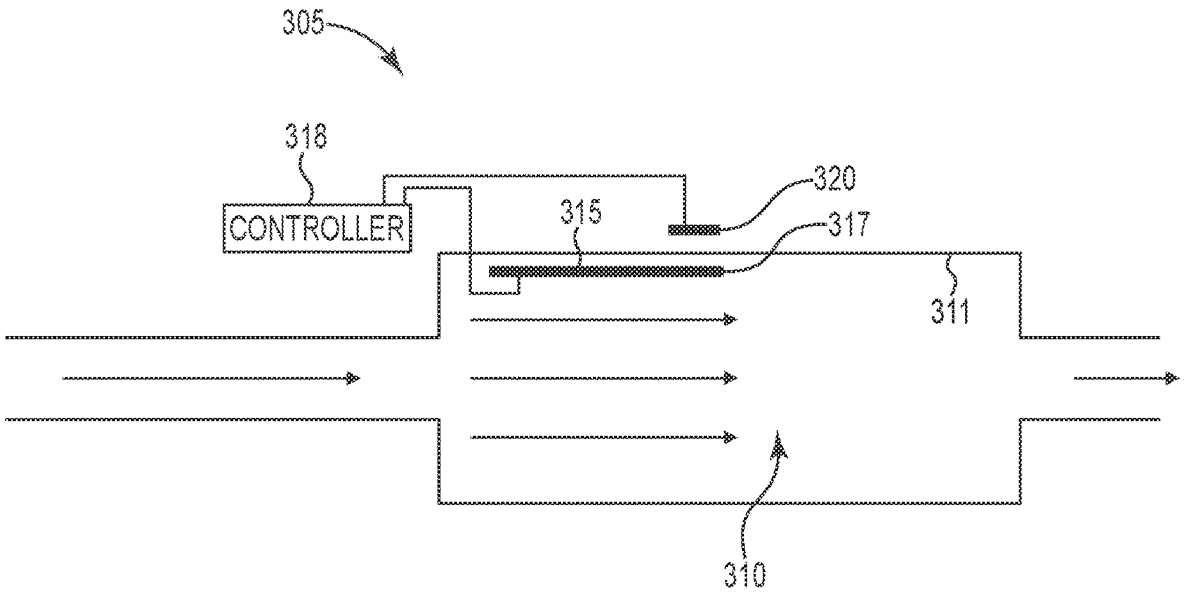
FIG. 3A is a top view of an example of a flow rate sensor having a magnet and a receive coil in a first position, in accordance with one or more embodiments of the present disclosure.

FIG. 3A is a top view of an example of a flow rate sensor 305 having a magnet 320 and a sensing coil 317 in a first position, in accordance with one or more embodiments of the present disclosure. The flow rate sensor 305 can further include a flow chamber 310, an inner surface 311 of the flow chamber 310, and a controller 318.

Similar to FIG. 2, the flow rate sensor 305 can be connected to a pipe sampling network. For example, the flow chamber 310 can be connected to the pipe sampling network such that gas is allowed to flow from the pipe sampling network and through the flow chamber 310 of the flow rate sensor 305.

The flow rate sensor 305 can include a magnet 320. The magnet 320 can be an object that produces a magnetic field.

The flow rate sensor 305 can further include a sensing coil 317 having a flexible base 315. The sensing coil 317 having the flexible base 315 can be located inside the flow chamber 310. The sensing coil 317 can be an electrical conductor in the shape of a coil where, upon application of an electric current, the coil can generate a magnetic field. The flexible base 315 can be a flexible PCB, and the sensing coil 317 can be located on the flexible PCB. The flexible PCB can be a polyimide flat flex PCB.

As illustrated in FIG. 3A, the sensing coil 317 having the flexible base 315 can be at the first position. At the first position, the flexible base 315 can be located proximate to the inner surface 311 of the flow chamber 310. In the first position, the sensing coil 317 and the flexible base 315 do not substantially interact with the flow of the gas through the flow chamber 310, as they are oriented in a direction substantially similar to the flow direction of the gas through the flow chamber 310. That is, the orientation of the sensing coil 317 and the flexible base 315 at the first position is substantially parallel to the flow direction of the gas through the flow chamber 310.

As illustrated in FIG. 3A, the sensing coil 317 with the flexible base 315 are located inside the flow chamber 310, whereas the magnet 320 is located outside of the flow chamber 310. However, embodiments of the present disclosure are not so limited. For example, the magnet 320 can be located inside the flow chamber 310, be integrated within the body of the flow chamber 310, etc.

As illustrated in FIG. 3, the sensing coil 317 and the magnet 320 can be electrically connected to the controller 318. Accordingly, the sensing coil 317 and the magnet 320 can transmit signals to and/or receive signals from the controller 318.

For example, the controller 318 can cause a direct current (DC) voltage to be applied to the sensing coil 317. The sensing coil 317 can accordingly receive the DC voltage from the controller 318 for the purpose of controlling the displacement of the coil with respect to the magnet. Additionally, there can be an AC voltage in addition to the DC voltage applied to the sensing coil 317 which can provide a mechanism for detecting the displacement of the coil from the magnet. Such a mechanism for measurement of the coil inductance can be indicative of proximity to the metallic component of the magnet.

To detect the aforementioned inductance, the signal from the controller 318 can be an oscillating AC voltage signal having a high impedance and high frequency. For example, the AC voltage can be applied having an impedance of 100 ohms and a frequency of 10 MHz, among other examples.

As a result of the application of the DC voltage to the sensing coil 317, the magnet 320 can cause the sensing coil 317 having the flexible base 315 to deflect from the first position to a second position. In the second position, the receive coil can more substantially interact with the flow of gas through the flow chamber 310, allowing for the determination for the flow rate of the gas through the flow chamber 310, as is further described in connection with FIG. 3B.

Figure 3B:
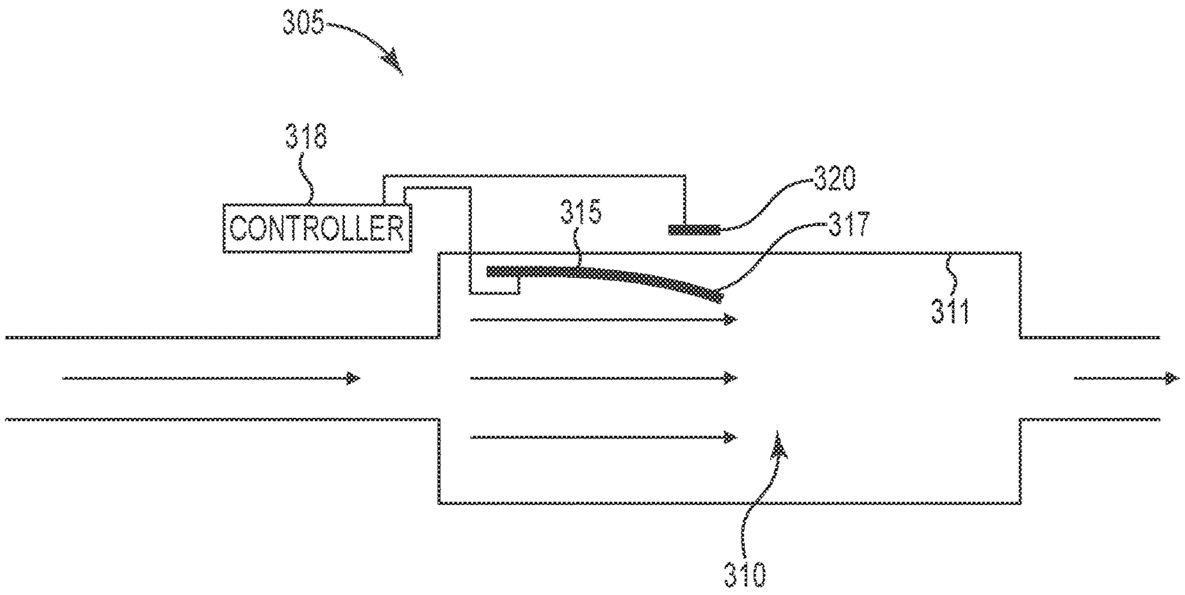
FIG. 3B is a top view of an example of a flow rate sensor having a magnet and a receive coil in a second position, in accordance with one or more embodiments of the present disclosure.

FIG. 3B is a top view of an example of a flow rate sensor 305 having a magnet 320 and a sensing coil 317 in a second position, in accordance with one or more embodiments of the present disclosure. The flow rate sensor 305 can further include the flow chamber 310, the inner surface 311 of the flow chamber 310, and the controller 318.

As mentioned above, as a result of the application of the DC voltage to the sensing coil 317, the magnet 320 can cause the sensing coil 317 having the flexible base 315 to deflect from the first position (e.g., as previously illustrated in FIG. 3A) to a second position (e.g., as illustrated in FIG. 3B). When the sensing coil 317 having the flexible base 315 is at the second position, the sensing coil 317 having the flexible base 315 protrudes away from the inner surface 311 of the flow chamber 310 and into the flow of gas through the flow chamber 310. The application of the DC voltage to the sensing coil 317 causes the sensing coil 317 to be repelled away from the magnet 320 as a result of magnetic opposition with the magnet 320.

As discussed, application of the DC voltage to the sensing coil 317 can cause the sensing coil 317 to protrude a particular distance (e.g., away from the inner surface 311) into the flow of gas. At the same time, the gas flowing through the flow chamber 310 can exert a force on the sensing coil 317 when the receive coil protrudes into the flow of gas in the flow chamber 310. For example, the orientation of the sensing coil 317 and the flexible base 315 at the second position is no longer substantially parallel to the flow direction of the gas through the flow chamber 310 like it was in the first position; rather, the sensing coil 317 and the flexible base 315 protrude into the flow direction of the gas and the gas impinges upon the sensing coil 317 and the flexible base 315, providing a force that tries to push the sensing coil 317 and the flexible base 315 back to the first position (e.g., but which is counteracted by the magnetic opposition from the magnet 320. Accordingly, the applied DC voltage to the sensing coil 317 can have a relationship with an amount of force required to move the sensing coil 317 with the flexible base 315 to the second position, and as such, a flow rate of the gas through the flow chamber 310 can be inferred, as is further described herein.

As previously described above, the controller 318 can measure an amplitude of the applied AC voltage at the sensing coil 317. A predetermined amplitude threshold may be known such that when the measured amplitude at the sensing coil 317 meets and/or exceeds the threshold, the controller 318 determines the sensing coil 317 having the flexible base 315 is at the second position.

As such, the controller 318 can determine whether the measured amplitude of the AC voltage associated with the DC voltage while the flexible base 315 is at the second position exceeds the threshold amplitude amount. Accordingly, the controller 318 can determine, in response to the amplitude exceeding the threshold amplitude amount, the flow rate of the gas through the flow chamber 310 based on the DC voltage, as is further described herein.

Once the controller 318 has determined the measured amplitude exceeds the threshold amplitude amount, the controller 318 can determine a flow rate of the gas through the flow chamber 310 based on the applied DC voltage to the sensing coil 317. For example, the controller 318 can include a memory (e.g., not illustrated in FIG. 3B for clarity and so as not to obscure embodiments of the present disclosure). The memory can include a lookup table stored therein. Accordingly, the controller 318 can determine the flow rate by comparing the applied DC voltage to a plurality of DC voltages included in the lookup table and determining, based on the DC voltage matching a particular DC voltage in the lookup table, the flow rate to be a particular flow rate from the lookup table that is associated with the particular DC voltage.

For example, the lookup table may include a DC voltage of 2 Volts (V) with an associated flow rate of 10 Liters per minute (L/m) and a voltage of 3 V with an associated flow rate of 15 L/m. In response to the controller 318 determining the applied DC voltage to be 2 V, the controller 318 can compare the applied DC voltage (e.g., 2 V) to the plurality of DC voltages included in the lookup table (e.g., 2 V, 3 V, etc.) and determine, based on the applied DC voltage (e.g., 2 V) matching a DC voltage of the plurality of DC voltages in the lookup table (e.g., 2 V), the flow rate to be 10 L/m.

In some examples, the applied DC voltage may not match exactly those DC voltages of the plurality of DC voltages in the lookup table. For instance, the applied DC voltage may be 2.2 V. In some examples, the controller 318 can determine a DC voltage of the plurality of DC voltages (e.g., 2 V) in the lookup table that is the closest to the applied DC voltage (e.g., 2.2 V), and determine the flow rate to be 10 L/m.

Additionally, in some examples, the closest frequency may not result in the accuracy desired and/or mandated in determining the flow rate. In some examples, the controller 318 can interpolate between those DC voltages of the plurality of DC voltages in the lookup table to determine an exact flow rate. For example, the applied DC voltage may be 2.4 V, and the controller 318 can interpolate, using the two closest DC voltages of the plurality of frequencies (e.g., 2 V and 3 V) to the applied DC voltage, to determine the flow rate associated with the applied DC voltage of 2.4 V to be approximately 12 L/m.

As described above, the resulting amplitude of the DC voltage applied to the sensing coil 317 can represent an amount of force required to deflect and hold the sensing coil 317 having the flexible base 315 in the gas flow, and as such, the flow rate can be inferred from the applied DC voltage to the sensing coil 317. Accordingly, if the flow rate of the gas through the flow chamber 310 increases, additional force would be required to keep the sensing coil 317 with the flexible base 315 at the second position (e.g., in the gas flow), and as such, the applied DC voltage to the sensing coil 317 would have to be increased.

Accordingly, if the flow rate were to increase, the amplitude would no longer exceed the threshold amplitude amount. As such, in response to the amplitude not exceeding the threshold amplitude amount, the controller 318 can adjust the DC voltage (e.g., increase the DC voltage) applied to the sensing coil 317 to a revised DC voltage, where at the revised DC voltage, the measured amplitude exceeds the threshold amplitude amount. Utilizing the lookup tables, the controller 318 can then determine the flow rate utilizing the revised DC voltage. Accordingly, such an approach can be utilized to determine the flow rate of the gas through the flow chamber 310, even if the flow rate changes.

Flow rate detection for an aspirating smoke detection system, according to the present disclosure, can allow for a flow rate sensor to be utilized for flow rate detection. The flow rate sensor can be easy to manufacture and implement in new and/or existing aspirating smoke detection systems. Such an approach can allow for a cheaper and easier to install flow rate sensor, as compared with previous approaches.

Figure 4:
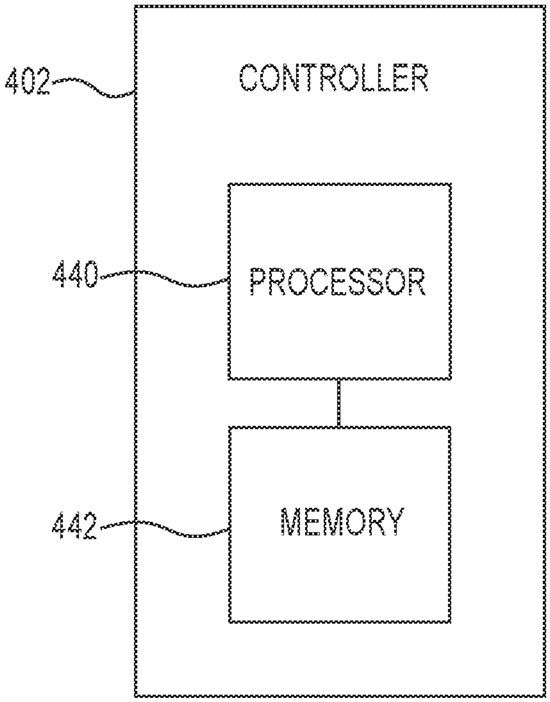
FIG. 4 is a controller for flow rate detection for an aspirating smoke detection system, in accordance with one or more embodiments of the present disclosure.

FIG. 4 is a controller 402 for flow rate detection for an aspirating smoke detection system, in accordance with one or more embodiments of the present disclosure. As illustrated in FIG. 4, the controller 402 can include a memory 442, and a processor 440 for flow rate detection for an aspirating smoke detection system in accordance with the present disclosure.

The memory 442 can be any type of storage medium that can be accessed by the processor 440 to perform various examples of the present disclosure. For example, the memory 442 can be a non-transitory computer readable medium having computer readable instructions (e.g., computer program instructions) stored thereon that are executable by the processor 440 for flow rate detection for an aspirating smoke detection system in accordance with the present disclosure. The computer readable instructions can be executable by the processor 440 to redundantly perform flow rate detection for an aspirating smoke detection system.

The memory 442 can be volatile or nonvolatile memory. The memory 442 can also be removable (e.g., portable) memory, or non-removable (e.g., internal) memory. For example, the memory 442 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical storage, and/or a magnetic medium such as magnetic cassettes, tapes, or disks, among other types of memory.

Further, although memory 442 is illustrated as being located within controller 402, embodiments of the present disclosure are not so limited. For example, memory 442 can also be located internal to another computing resource (e.g., enabling computer readable instructions to be downloaded over the Internet or another wired or wireless connection).

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A flow rate sensor for an aspirating smoke detection system, comprising:
- a flow chamber configured to allow a gas to flow through the flow chamber;
- a bluff body located inside the flow chamber and configured to disrupt the flow of the gas through the flow chamber;
- a receive coil located on a printed circuit board (PCB) inside the flow chamber, wherein:
  - the receive coil is configured to physically oscillate in response to the flow of the gas acting upon the receive coil; and
  - in response to the physical oscillation, the receive coil is configured to generate a signal;
- a memory; and
- a processor configured to execute executable instructions stored in the memory to:
  - determine a frequency of the signal generated by the receive coil; and
  - determine a flow rate of the gas through the flow chamber based on the frequency of the signal.

2. The flow rate sensor of claim 1, wherein the processor is configured to determine the flow rate by:
- comparing the frequency of the signal to a plurality of frequencies included in a lookup table; and
- determining, based on the frequency matching a particular frequency of the plurality of frequencies included in the lookup table, the flow rate to be a particular flow rate from the lookup table that is associated with the particular frequency.

3. The flow rate sensor of claim 1, wherein the flow rate sensor further includes a transmit coil.

4. The flow rate sensor of claim 3, wherein the processor is configured to cause an oscillating signal to be applied to the transmit coil such that the receive coil generates the signal in response to the physical oscillation of the receive coil.

5. The flow rate sensor of claim 3, wherein the transmit coil is an electromagnet located on a printed circuit board.

6. The flow rate sensor of claim 1, wherein the signal generated by the receive coil is an amplitude modulated signal.

7. The flow rate sensor of claim 1, wherein the processor is configured to demodulate the signal generated by the receive coil to determine the frequency.

8. The flow rate sensor of claim 1, wherein the bluff body is configured to cause the gas flowing through the flow chamber to be a turbulent flow in the flow chamber.

9. The flow rate sensor of claim 1, wherein the receive coil is located downstream of the bluff body in the flow chamber.

* * * * *